United States Patent [19]

Ogawa et al.

[11] 4,028,392
[45] June 7, 1977

[54] ISOCYANATE PREPOLYMERS

[75] Inventors: Shinsaku Ogawa; Akira Ide; Kazurou Komatsu; Sojiro Matsumoto; Yasushi Kishimoto, all of Nebeoka, Japan

[73] Assignee: Asahi Kasei Kogyo Kabushiki Kaisha, Osaka, Japan

[22] Filed: May 20, 1975

[21] Appl. No.: 579,180

[30] Foreign Application Priority Data

May 20, 1974 Japan .............................. 49-56355

[52] U.S. Cl. .................... 260/453 AR; 260/453 A; 260/453 AB; 260/453 AL
[51] Int. Cl.² .......... C07C 119/042; C07C 119/045; C07C 119/048
[58] Field of Search ... 260/453 AB, 453 A, 453 AR, 260/453 AL

[56] References Cited

UNITED STATES PATENTS

| | | | |
|---|---|---|---|
| 3,124,605 | 3/1964 | Wagner | 260/453 AB |
| 3,903,127 | 9/1975 | Wagner | 260/453 AB |

Primary Examiner—Dolph H. Torrence
Attorney, Agent, or Firm—Sughrue, Rothwell, Mion, Zinn & Macpeak

[57] ABSTRACT

An isocyanate prepolymer represented by the formula

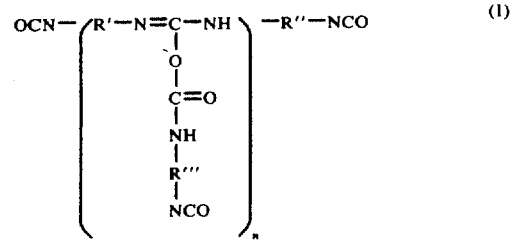

wherein $n$ is an integer of 1 to 6, R', R'' and R''', which may be the same or different, each represents a divalent aliphatic, araliphatic, aromatic or acyclic group which may contain a

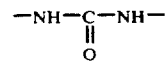

bond, and R'' and R''' may contain a

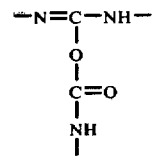

bond, and a process for producing the same.

6 Claims, No Drawings

ISOCYANATE PREPOLYMERS

BACKGROUND OF THE INVENTION

1. Field of the Invention

This invention relates to an isocyanate prepolymer and a process for producing the same. More particularly, this invention relates to an isocyanate prepolymer having at least three isocyanate groups represented by the formula (I) above and an improved process for producing the same.

2. Description of the Prior Art

Hitherto, it is well known that compounds having a biuret structure represented by the formula

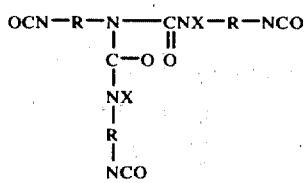

wherein X represents a hydrogen atom or a

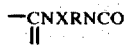

group and R is an aliphatic, hydroaromatic, araliphatic including aralkyl or aromatic group which may or may not be substituted with Cl, $NO_2$, an alkyl group, an alkoxy group or the like, can be prepared by reacting at least 3 moles of an organic diisocyanate with 1 mole of water in the absence of solvents, as disclosed in U.S. Pat. No. 3,124,605.

However, it was found that, although a diisocyanate generally reacts with water, a reaction system consisting of the diisocyanate and water temporarily forms an emulsion because of a low mutual solubility between the diisocyanate and water, and in such an emulsion system the compounds having the above biuret structure can only be produced by the reaction between the diisocyanate and water dissolved in a small amount in the diisocyanate phase. It was also found that the reaction between water and the diisocyanate dissolved in a small amount in the aqueous phase does not produce the desired compounds having a biuret structure but results in predominantly a polymer having the formula

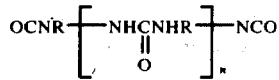

wherein R is as defined above and n is an integer of 1 or more, as a precipitate.

A polyisocyanate having a biuret structure is a liquid at room temperature (e.g. about 20° to 30° C) and, by taking advantage of this, is useful as a raw material for urethane paint. However, the formation of a polyurea precipitate as a by-product associated necessarily with a polyisocyanate having a biuret structure adversely affects its utility and also makes the product remarkably less valuable. The polyurea is produced by the mechanism described above and generally is produced in an amount more than about 0.5% by weight based on the amount of the compound having a biuret structure, although the amount of the polyurea produced markedly varies depending upon the reaction temperature, the stirring rate used during the reaction, and the ratio of diisocyanate and water.

Of course, the amount of the polyurea produced as a by-product can be minimized if a large amount, i.e., more than 40 moles, of an diisocyanate is used per mole of water but the formation of the polyurea can not be avoided completely. Further, under such reaction conditions, a large excess of the diisocyanate must be separated from the compound having a biuret structure upon completion of the reaction and, therefore, a pure compound having a biuret structure can not be obtained economically.

Also, since the conventional process for producing a compound having a biuret structure is affected by the mutual solubility and the mutual solubilizing rate of the reactants in an emulsion state formed temporarily in view of its reaction mechanism as well as by the surface area of the emulsion phase, the molecular weight distribution of the compound having a biuret structure produced tends to be broad and, as a result, a compound having a biuret structure having a low molecular weight and a low viscosity can not be easily obtained.

SUMMARY OF THE INVENTION

An object of this invention is to provide a novel isocyanate prepolymer.

Another object of this invention is to provide a process for producing an isocyanate prepolymer in which the precipitation of polyurea does not occur.

A further object of this invention is to provide a process for producing an isocyanate prepolymer of high quality, with minimum coloration in which the reaction rate can be increased.

Still another object of this invention is to provide an isocyanate prepolymer having a novel structure, a narrow molecular weight distribution, a low molecular weight and a low viscosity.

These and other objects of this invention are achieved in one embodiment with an isocyanate prepolymer represented by the formula

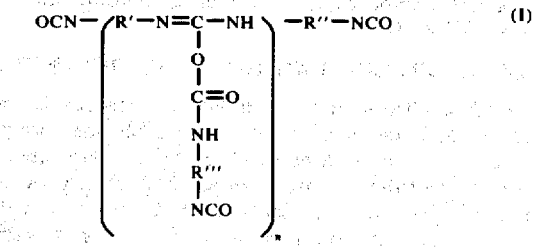

wherein n is an integer of 1 to 6, R', R'' and R''', which may be the same or different, each represents a divalent aliphatic, araliphatic, aromatic or acyclic group which may contain a $$-NH-\underset{\underset{O}{\|}}{C}-NH-$$

bond, and R'' and R''' may contain a

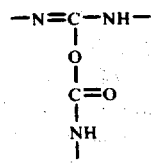

bond.

These and other objects are achieved in a second embodiment of this invention providing a process for producing an isocyanate prepolymer represented by the formula

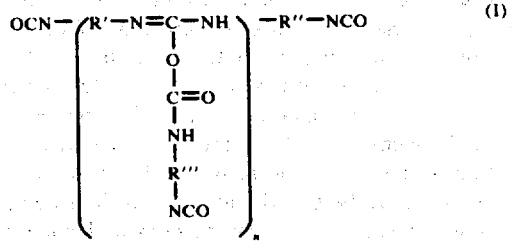

wherein $n$ is an integer of 1 to 6, R', R'' and R''', which may be the same or different, each represents a divalent aliphatic, araliphatic, aromatic or acyclic group which may contain a

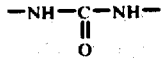

bond, and R'' and R''' may contain a

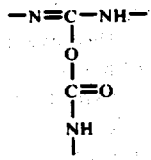

bond, which comprises reacting water with a diisocyanate in an amount of 5 to 40 moles per mole of water in a hydrophilic organic solvent at a temperature of from 70° to 200° C.

DETAILED DESCRIPTION OF THE INVENTION

As a result of extensive studies on a process for preparing an isocyanate prepolymer which does not produce a polyurea as a by-product, it was found that the formation of the polyurea can be completely prevented by conducting the reaction in the presence of a hydrophilic organic solvent in an amount sufficient to form a homogeneous mixture of a diisocyanate and water throughout the entire period of the reaction. This invention is based on the above finding.

The process of this invention not only prevents the formation of a polyurea as a by-product but also provides an isocyanate prepolymer having a narrow molecular weight distribution and also provides, by employing specific reaction conditions, an isocyanate prepolymer having a low viscosity and low molecular weight suitable for use in paints.

Analysis of the chemical structure of the isocyanate prepolymer according to the present invention clearly demonstrated differences from that of the prepolymer obtained using the conventional process.

That is, in the conventional process, a urea bond

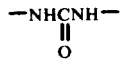

is temporarily formed in the product via the reaction between 2 moles of a diisocyanate and 1 mole of water, and each of these reactive hydrogen atoms in the urea bond further reacts with the diisocyanate to form a compound having a biuret structure represented by the formula

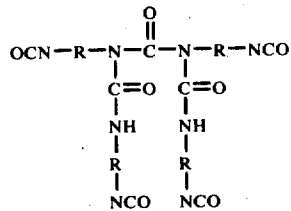

wherein R is as defined above.

The hydrogen atoms contained in the resulting compound having a biuret structure are also reactive and are considered to further react with the diisocyanate. Thus, the reaction of the conventional process is considered to take place between more than 3 moles of a diisocyanate and 1 mole of water.

On the other hand, it has now been found that the urea bond formed temporarily via the reaction between 2 moles of a diisocyanate and 1 mole of water produces a compound of the formula

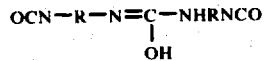

wherein R is as defined above, through a keto-enal rearrangement, and the hydrogen atom in the alcohol group of the resulting compound further reacts with the diisocyanate. As is apparent from the above reaction mechanism, more than 1 mole of a diisocyanate can not be reacted with one urea bond.

In further polymerization of the above compound, the terminal isocyanate groups react first with water and then with a diisocyanate, and the urea bond thus formed either further reacts with a diisocyanate or is polymerized, without further reactions in the above manner, to form the compounds having the above formula (I).

Accordingly, in the process of this invention, although the isocyanate is used in an amount of about 5 to 40 moles per mole of water, the diisocyanate does not react with water in a molar ratio of more than 3 moles of the diisocyanate per mole of water as is the situation in the conventional process, and the compounds of this invention represented by the formula (I) above can be produced via a reaction of 1 mole of water with at most 3 moles of a diisocyanate but at least 1 mole of a diisocyanate.

The fact that the compounds of this invention have the formula (I) above can be explained with reference to a wide variety of compounds, e.g., as described hereinafter, but for the sake of simplicity, reference is made hereinafter to hexamethylene diisocyanate as a representative diisocyanate raw material.

First, the difference between known compounds having a biuret structure and the compounds of this invention can be noted in the correlation between the molecular weight of the prepolymer produced and the isocyanate group content per unit weight. The compound having a biuret structure is produced via the reaction of at least 3 moles of hexamethylene diisocyanate with 1 mole of water and, therefore, as is apparent from the formula, the isocyanate group content per molecule is high.

On the other hand, the isocyanate prepolymer of this invention is produced by a reaction of 1 mole of water with at most 3 moles of hexamethylene diisocyanate and, therefore, the isocyanate group content per molecule is lower than that of the compounds having a biuret structure. This difference is summarized in Table 1 below.

content, 24.5% by weight) obtained in accordance with the present invention is analyzed using a high performance mass spectrometer, Model JSM-D 100 (manufactured by Japan Electron Optics Laboratory Co., Ltd.) at an ionizing voltage of 75 eV, a markedly strong fragment corresponding to the group

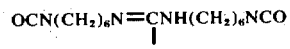

was observed in the mass spectrum. The formation of this fragment can be easily expected from the structure of the formula (I) of this invention as the result of the cleavage of a urethane bond

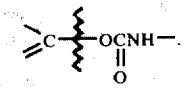

Table 1

| | Biuret Structure Compound | | | | | Compounds of Present Invention | | | | |
|---|---|---|---|---|---|---|---|---|---|---|
| | Amount of Water (mole) | Amount of Hexa-methylene Diisocyanate (mole) | Molecular Weight | Number of Isocyanate Groups in Molecule | Amount of Isocyanate Groups (% by weight) | Amount of Water (mole) | Amount of Hexamethylene Diisocyanate (mole) | Molecular Weight | Number of Isocyanate Groups in Molecule | Amount of Isocyanate Groups (% by weight) |
| Trimer | 1 | 3 | 478 | 3 | 26.3 | 1 | 3 | 478 | 3 | 26.3 |
| Tetramer | 1 | 4 | 646 | 4 | 25.9 | 2 | 4 | 620 | 3 | 20.4 |
| Pentamer | 1 | 5 | 814 | 5 | 25.8 | 2 | 5 | 788 | 4 | 21.3 |
| | | | | | | 3 | 5 | 762 | 3 | 16.5 |
| Hexamer | 1 | 6 | 962 | 6 | 25.7 | 3 | 6 | 930 | 4 | 18.1 |
| | | | | | | 4 | 6 | 904 | 3 | 13.9 |

As shown in Table 1, the compounds of this invention are clearly distinguishable from the compounds having a biuret structure. In particular, an apparent difference can be noted in the ratio of the number of moles of water and the number of moles of the diisocyanate in the reaction product. When an average molecular weight and an average isocyanate group content of the isocyanate prepolymer produced in accordance with the process of this invention are determined, respectively, using procedures conventionally used, neither of these values agrees with the correlation between the average molecular weight and the average isocyanate group content expected from compounds having a biuret structure, and the compounds of this invention can be recognized as having the chemical structure represented by the formula (I) since the analytical values of the compounds correspond to the values expected from the formula (I).

A second method for identifying the compounds of this invention is an infrared spectral analysis. That is, from the structure represented by the formula (I), a urethane bond

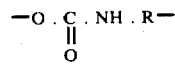

is expected to be present in the molecule, and the infrared spectrum of the isocyanate prepolymer clearly shows characteristic absorptions at 1680 cm$^{-1}$ and 1540 cm$^{-1}$ which are completely consistent with those shown in usual urethanes, for example, a urethane obtained from butanol and hexamethylene diisocyanate, and which are not shown in the infrared spectrum of a compound having a biuret structure.

A third method for identifying the compounds of this invention is mass spectral analysis. When an adduct of hexamethylene diisocyanate and water (isocyanate On the other hand, since the cleavage of an N—C bond may first occur in the biuret structure, the presence of the above fragment can not be explained unless a simultaneous cleavage of a carbonyl group >C=O occurs which is difficult to cleave due to strong bonding.

The facts described above clearly support the chemical structure of the formula (I) of this invention.

The present invention has been described with reference to hexamethylene diisocyanate as a specific embodiment of a diisocyanate for simplicity, but it is to be understood that the situation described above would be common to other diisocyanates, and the significance of the formula (I) will be apparent to one skilled in the art from the above description.

Also, it is to be understood that in the conventional process the production of a pure trimer represented by the formula (I) is extremely difficult and, in fact, the product obtainable by the conventional process generally contains a substantial amount of a dimer and a tetramer as well as higher polymers. However, the process of this invention makes it possible to produce a purer trimer product, i.e., a product comprising predominantly the desired trimer.

Examples of suitable diisocyanates which can be used in the present invention are aliphatic diisocyanates such as ethylene diisocyanate, tetramethylene diisocyanate, hexamethylene diisocyanate, 2,6-diisocyanate methylcaproate and the like, araliphatic diisocyanates such as xylene diisocyanate and the like, aromatic diisocyanates such as toluene diisocyanate, meta-phenylene diisocyanate and the like, acyclic diisocyanates such as cyclohexane-1,4-diisocyanate and the like, or a mixture thereof.

Of the aliphatic diisocyanates, unsaturated hydrocarbon diisocyanates tend to have a poor weather-resistance property due to the presence of double bonds. Also, the aromatic diisocyanates which contain only aromatic groups as R', R'' and R''' groups shows a slightly poor weather-resistance property as compared with that of the araliphatic diisocyanates and the isocyanate prepolymer produced from the aromatic diisocyanates has a tendency of yellowing. Thus, from the standpoint of the utility of the diisocyanate prepolymer hereinafter described, the aliphatic diisocyanates, in particular, saturated hydrocarbon diisocyanates are preferred in the present invention.

The hydrophilic organic solvents which can be used in the present invention are, as will be apparent from the reaction methanism described above, those capable of dissolving both water and the diisocyanate starting material and forming a homogeneous phase under the reaction conditions used. These organic solvents are preferably used in an amount sufficient to form a homogeneous reaction system.

The amount of these hydrophilic organic solvents which can be used in the reaction varies widely depending upon the type of the diisocyanates and the solvents used, but in a specific example, e.g., a combination of hexamethylene diisocyanate as a diisocyanate and trimethyl phosphate as a hydrophilic organic solvent, the solvent can be in an amount of from about 0.1 to about 20 parts by weight, preferably 0.3 to 3 parts by weight, per part by weight of the hexamethylene diisocyanate. The solvents in which water is only slightly soluble are not preferred from an economical standpoint since such solvents must be used in a large amount in order to form a homogeneous reaction system thereby increasing the amount of solvent to be recovered upon completion of the reaction. The solubility of water in the solvents preferably is more than about 0.5% by weight. Accordingly, benzene, toluene, monochlorobenzene, dichlorobenzene, etc. are not preferred. Also, in view of the fact that an isocyanate group is a functional group having a high reactivity with various groups, solvents which are reactive with an isocyanate group should be avoided even if the solvents are hydrophilic. For example, amines, alcohols, carboxylic acids, phosphoric acids, diketones, etc. are not appropriate for use in this invention.

In the process of this invention, the use of an alkaline reaction system having a pH higher than about 9 is not preferred due to side reactions, for example, the formation of a cyanuric ring, i.e., 2,4,6-triisocyanate isocyanurate ring. Accordingly, the use of strongly basic solvents such as pyridine is not preferred. The reaction of the present invention can be preferably carried out at a pH value of 1 to 9.

Further, solvents which tend to increase the coloration of the product in the presence of an isocyanate group are not preferred and, thus, preferably the solvents should be chemically stable.

Still further, the solvents are preferably those having a boiling point not markedly below the boiling point of water but, taking into consideration the subsequent recovery of the solvents, the solvents preferably have a boiling point below that of the isocyanate prepolymer, a preferred boiling point of the solvents being in the range of from about 80° to about 200° C.

Examples of suitable hydrophilic solvents which satisfy the above requirements are carboxylic acid esters, phosphoric acid esters amides, ketones, nitriles, ethers and the like. Particularly preferred examples of suitable solvents are methyl cellosolve acetate, cellosolve acetate, methyl isobutyl ketone, trimethyl phosphate, dimethylformamide, propionitrile, adiponitrile, cyclohexanone, diethylene glycol dimethyl ether and the like. In particular, methyl cellosolve and trimethyl phosphate are preferred because of their excellent anti-coloring properties.

These hydrophilic solvents are used in such an amount that a mixture of the hydrophilic solvent, water and a diisocyanate forms a homogeneous phase under the reaction conditions employed.

With respect to the molar ratio of water and the diisocyanate, the molecular weight of the polyisocyanate prepolymer increases as the amount of the diisocyanate decreases. The use of a large amount of the diisocyanate is preferred since the molecular weight of the isocyanate prepolymer decreases and the viscosity of the prepolymer decreases, but, on the other hand, the amount of unreacted diisocyanate to be recovered after completion of the reaction increases and this is economically disadvantageous. Accordingly, the molar ratio of water and the diisocyanate used in the reaction is preferably 5 to 40 moles of the diisocyanate per mole of water.

The reaction temperature is preferably 70° C to 200° C. At a temperature below 70° C, a urea bonding can occur but the reaction for side chain formation tends to take place with difficulty. At a temperature above 200° C, the reaction mixture tends to be colored and is not preferred.

After completion of the reaction, it is advantageous to recover any excess of the diisocyanate and the hydrophilic solvent from the reaction mixture at as early a stage as is possible and at a temperature as low as possible. The presence of excess diisocyanate and the hydrophilic solvent in the reaction mixture at a high temperature for a long period of time results in the formation of high molecular weight compounds and/or a colored product. Thus, the excess of the unreacted diisocyanate and the hydrophilic solvent can be advantageously recovered using a falling film evaporation drum or a molecular still.

The content of the unreacted diisocyanate remaining in the isocyanate prepolymer produced is preferably less than about 0.5% by weight after the recovery as described above. If the content of the diisocyanate remaining in the reaction system exceeds about 0.5% by weight, the product sometimes has an unpleasant odor and exhibits an undesirable toxicity such as giving rise to skin eruptions.

In the above reaction between water and a diisocyanate, coloration inhibitors, polymerization inhibitors, ultraviolet light stabilizers, catalysts and the like which are all well known in the art for the production of polyisocyanates can be incorporated into the reaction system.

As described previously, the reaction of the present invention is effected in a homogeneous phase using a hydrophilic organic solvent. Some of the important advantages which are realized by these reaction conditions are hereinafter described in detail.

1. In the process according to the present invention, the precipitation of polyurea can be prevented. This advantage appears to be beneficial in the production of isocyanate prepolymers on an industrial scale, since the formation of scale can be prevented and the necessity of filtration of the reaction system during the reaction can be eliminated thereby making it possible to operate the process continuously for a long period of time.

2. In the process of this invention, the reaction rate can be generally increased and a product of high quality with minimum coloration and degradation can be easily obtained.

3. In the product of this invention, a narrow molecular weight weight distribution can be achieved as described previously. As the purity of the trimer increases, the molecular weight and the viscosity of the product generally decreases. When such as isocyanate prepolymer is used in a paint, such a prepolymer is preferred since the viscosity of the paint decreases and a large amount of inexpensive alcohols can be incorporated into the paint relative to the decrease in the viscosity. In contrast, in the conventional production of isocyanate prepolymers, the reaction proceeds in a heterogeneous system, and a broad molecular weight distribution in the resulting product necessarily occurs. A relatively large amount of tetramer is present in the product, and pure trimer is difficult to obtain. The process of this invention makes it possible to produce isocyanate prepolymers having a narrow molecular weight distribution and, thus, a prepolymer having a low molecular weight and a low viscosity can be easily obtained.

The present invention is further illustrated in greater detail by the following examples, but these examples are given for illustrative purposes only and are not to be construed as limiting the invention. Unless otherwise indicated, all parts, percents, ratios, and the like are by weight.

EXAMPLE 1

18 g of water, 1680 g of hexamethylene diisocyanate and 600 g of trimethyl phosphate were mixed at room temperature (i.e., 20°–30° C) to obtain a homogeneous mixture, and the resulting homogeneous liquid was then allowed to react in a reactor equipped with a reflux condenser at a temperature of 160° C for 60 minutes under atmospheric pressure. The resulting reaction mixture was found to be substantially free from any precipitated materials. The reaction mixture was evaporated under a reduced pressure of 5 mmHg at a temperature of 160° C using a falling film evaporation drum followed by heating under a reduced pressure of 0.2 mmHg at a temperature of 180° C in a molecular still to recover unreacted hexamethylene diisocyanate and trimethyl phosphate by evaporation. The product thus obtained as a drum bottom (390 g) was found to have an unreacted hexamethylene diisocyanate content of less than 0.5%, a viscosity of 950 cps at 30° C, an average molecular weight of 510 and an isocyanate group content of 24.4%.

EXAMPLE 2

18 g of water, 2500 g of hexamethylene diisocyanate and 1500 g of methyl cellosolve acetate were mixed at room temperature to obtain a homogeneous mixture, and the resulting homogeneous liquid was then allowed to react in a reactor equipped with a reflux condenser at a temperature of 140° C for 120 minutes under atmospheric pressure. The resulting reaction mixture was worked up in a similar manner to Example 1 to recover the unreacted hexamethylene diisocyanate and the methyl cellosolve acetate. The product thus obtained as a drum bottom (361 g) was found to have an unreacted hexamethylene diisocyanate content of less than 0.5%, a viscosity of 1500 cps at 30° C, an average molecular weight of 530 and an isocyanate group content of 24.1%.

EXAMPLE 3

18 g of water, 700 g of hexamethylene diisocyanate and 700 g of dimethylformamide were mixed to obtain a homogeneous solution, and the resulting solution was then allowed to react in reactor equipped with a reflux condenser at a temperature of 130° C for 120 minutes under atmospheric pressure. The resulting reaction was found to be substantially free from any precipitated materials and was worked up in a similar manner to Example 1 to recover the unreacted hexamethylene diisocyanate and the dimethylformamide. The product thus obtained as a drum bottom (292 g) was found to have an unreacted hexamethylene diisocyanate content of less than 0.5%, a viscosity of 5200 cps at 30° C, an average molecular weight of 630 and an isocyanate group content of 22.3%.

EXAMPLE 4

18 g of water, 2100 g of tetramethylene diisocyanate and 700 g of trimethyl phosphate were mixed at room temperature to obtain a homogeneous mixture, and the resulting homogeneous liquid was then allowed to react and subjected to recovery of the unreacted tetramethylene diisocyanate in a similar manner to Example 1. The product thus obtained as a drum bottom (370 g) was found to have an unreacted tetramethylene diisocyanate content of less than 0.5%, a viscosity of 1100 cps at 30° C, an average molecular weight of 450 and an isocyanate content of 29.1%.

EXAMPLE 5

18 g of water, 2820 g of xylene diisocyanate and 1500 g of trimethyl phosphate were mixed to obtain a homogeneous mixture, and the resulting liquid was then allowed to react in a reactor equipped with a reflux condenser at a temperature of 130° C for 120 minutes. The resulting reaction mixture was found to be substantially free from any precipitated materials and was heat-evaporated under a pressure of 1 mmHg at a temperature of 230° C using a molecular still to recover the unreacted xylene diisocyanate and the solvent. The product thus obtained as a drum bottom (505 g) was found to have an unreacted xylene diisocyanate content of less than 0.5%, a viscosity of 75,000 at 30° C, an average molecular weight of 550 and an isocyanate group content of 22.5%.

While the invention has been described in detail and with reference to specific embodiments thereof, it will be apparent to one skilled in that art that various changes and modifications can be made therein without departing from the spirit and the scope thereof.

What is claimed is:

1. An isocyanate prepolymer represented by the formula

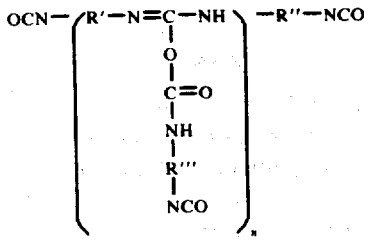

wherein n is an integer of 1 to 6; R', R" and R'" may be the same and each represents a divalent aliphatic, araliphatic, aromatic or acyclic group.

2. The isocyanate prepolymer according to claim 1, wherein R', R" and R'" each represents an alkylene group.

3. The isocyanate prepolymer according to claim 1, wherein R', R" and R'" each represents a hexamethylene group.

4. The isocyanate prepolymer according to claim 1, wherein R', R" and R'" each represents a divalent araliphatic group.

5. The isocyanate prepolymer according to claim 1, wherein R', R" and R'" each represents a xylylene group.

6. The isocyanate prepolymer according to claim 1, wherein R', R" and R'", which may be the same, each represents a divalent aliphatic group.

* * * * *